United States Patent
Morrison et al.

(10) Patent No.: US 10,675,422 B2
(45) Date of Patent: Jun. 9, 2020

(54) MONITORING RESPIRATORY PARAMETERS THROUGH ULTRASONIC MEASUREMENTS INDICATING FLOW CHANGES IN RESPIRATORY DRUG DELIVERY DEVICES

(71) Applicant: KONINKLIJKE PHILIPS N.V., Eindhoven (NL)

(72) Inventors: Mark Steven Morrison, Basking Ridge, NJ (US); Dirk Ernest Von Hollen, Clark, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 1172 days.

(21) Appl. No.: 14/903,734

(22) PCT Filed: Jun. 24, 2014

(86) PCT No.: PCT/IB2014/062551
§ 371 (c)(1),
(2) Date: Jan. 8, 2016

(87) PCT Pub. No.: WO2015/004554
PCT Pub. Date: Jan. 15, 2015

(65) Prior Publication Data
US 2016/0166787 A1 Jun. 16, 2016

Related U.S. Application Data
(60) Provisional application No. 61/844,013, filed on Jul. 9, 2013.

(51) Int. Cl.
*A61M 15/00* (2006.01)
*A61M 16/00* (2006.01)
(Continued)

(52) U.S. Cl.
CPC ...... *A61M 15/0093* (2014.02); *A61M 11/005* (2013.01); *A61M 11/06* (2013.01);
(Continued)

(58) Field of Classification Search
CPC ...... A61M 15/00–011; A61M 15/0028; A61M 15/0065–0078; A61M 15/009;
(Continued)

(56) References Cited

U.S. PATENT DOCUMENTS 5,794,612 A   8/1998  Wachter
5,894,841 A * 4/1999  Voges ............... A24F 47/008
                                              128/203.12
(Continued)

FOREIGN PATENT DOCUMENTS

EP     1441222 A2   7/2004
JP    2012127358 A  7/2012

*Primary Examiner* — Michael J Tsai
*Assistant Examiner* — Ned T Heffner
(74) *Attorney, Agent, or Firm* — Daniel H. Brean

(57) ABSTRACT

Systems and methods for delivering medicament to a subject use one or more sensors to generate signals that represent characteristics of the ultrasonic energy emitted into or by a respiratory medicament delivery device. Parameters based on these signals indicate energy amplitude in one or more frequency ranges. Such parameters can be used to determine respiratory parameters, patient adherence, and/or other parameters.

8 Claims, 17 Drawing Sheets

(51) Int. Cl.
 G01N 29/22 (2006.01)
 A61M 11/00 (2006.01)
 A61M 11/06 (2006.01)
 G01N 29/032 (2006.01)
 B05B 17/06 (2006.01)
 B05B 11/00 (2006.01)
 B65D 83/14 (2006.01)

(52) U.S. Cl.
 CPC ...... *A61M 15/009* (2013.01); *A61M 15/0013* (2014.02); *A61M 15/0016* (2014.02); *A61M 15/0085* (2013.01); *A61M 15/0086* (2013.01); *A61M 16/0051* (2013.01); *A61M 16/024* (2017.08); *G01N 29/032* (2013.01); *G01N 29/222* (2013.01); *A61M 15/0018* (2014.02); *A61M 15/0021* (2014.02); *A61M 15/0065* (2013.01); *A61M 15/0091* (2013.01); *A61M 16/0096* (2013.01); *A61M 2016/0015* (2013.01); *A61M 2016/0036* (2013.01); *A61M 2205/0294* (2013.01); *A61M 2205/3334* (2013.01); *A61M 2205/3358* (2013.01); *A61M 2205/3375* (2013.01); *A61M 2205/50* (2013.01); *A61M 2205/505* (2013.01); *A61M 2205/581* (2013.01); *A61M 2205/582* (2013.01); *A61M 2205/583* (2013.01); *B05B 11/30* (2013.01); *B05B 17/06* (2013.01); *B65D 83/14* (2013.01); *G01N 2291/02836* (2013.01)

(58) Field of Classification Search
 CPC .. A61M 15/0093; A61M 15/06; A61M 15/08; A61M 15/085; A61M 11/00; A61M 11/001–008; A61M 11/02–08; A61M 13/00; A61M 2205/3345; A61M 2205/3375; A61M 2205/505; A61M 2205/52; A61M 2230/40
 See application file for complete search history.

(56) References Cited

U.S. PATENT DOCUMENTS

| | | | |
|---|---|---|---|
| 6,192,876 B1 * | 2/2001 | Denyer | A61B 5/087 128/204.18 |
| 8,960,189 B2 | 2/2015 | Morrison | |
| 2010/0269821 A1 | 10/2010 | Larsson | |
| 2011/0041847 A1 | 2/2011 | Cosic | |
| 2011/0226235 A1 | 9/2011 | Morrison | |
| 2011/0226237 A1 | 9/2011 | Morrison | |
| 2012/0055472 A1 | 3/2012 | Brunnberg | |
| 2012/0312302 A1 * | 12/2012 | Cardelius | A61M 16/024 128/203.14 |
| 2013/0008436 A1 | 1/2013 | Von Hollen | |
| 2013/0186392 A1 | 7/2013 | Haartsen | |
| 2016/0250426 A1 | 9/2016 | Morrison | |

* cited by examiner

MONITORING RESPIRATORY PARAMETERS THROUGH ULTRASONIC MEASUREMENTS INDICATING FLOW CHANGES IN RESPIRATORY DRUG DELIVERY DEVICES

CROSS-REFERENCE TO RELATED APPLICATIONS

This patent application claims the priority benefit under 35 U.S.C. § 371 of international patent application no. PCT/IB2014/062551, filed Jun. 24, 2014, which claims the priority benefit under 35 U.S.C. § 119(e) of U.S. Provisional Application No. 61/844,013 filed on Jul. 9, 2013, the contents of which are herein incorporated by reference.

BACKGROUND

1. Field

The present disclosure pertains to systems and methods that measure ultrasonic energy emitted during the use of respiratory therapy delivery devices, and, in particular, to monitor respiratory parameters and/or patient adherence based thereon.

2. Description of the Related Art

Respiratory therapy delivery devices include respiratory drug delivery devices. Respiratory therapy delivery devices are used to treat many types of patients. As used herein, respiratory drug delivery devices may be referred to as respiratory medicament delivery devices. Some types of respiratory drug delivery devices, for example nebulizers, may include components that mechanically move at frequencies in the ultrasonic range. Device performance may depend on controlling the operation and/or timing of such devices with sufficient accuracy and efficacy. Positive treatment outcomes may depend on many factors, including patient adherence.

SUMMARY

Accordingly, one or more embodiments provide a system configured to deliver medicament to a subject. The system comprises a respiratory medicament delivery device, a source of ultrasonic energy, a sensor, and one or more processors configured to execute computer program modules. The respiratory medicament delivery device is configured to combine breathable gas and medicament for delivery to an airway of a subject. The respiratory medicament delivery device includes a valve configured to open responsive to respiratory actuation by the subject. The source of ultrasonic energy is configured to emit ultrasonic energy at an operating frequency such that at least some emitted ultrasonic energy enters the respiratory medicament delivery device. The sensor is configured to generate output signals conveying information related to one or more characteristics of the ultrasonic energy emitted by the source of ultrasonic energy. The computer program modules comprise a parameter determination module and a flow module. The parameter determination module is configured to determine, based on the generated output signals, a first parameter that indicates energy amplitude of emitted ultrasonic energy. The flow module is configured to detect one or more flow changes through the valve based on one or more changes of the first parameter. The one or more flow changes are responsive to respiratory actuation by the subject.

It is yet another aspect of one or more embodiments to provide a method of delivering medicament to a subject. The method comprises combining, by a respiratory medicament delivery device, breathable gas and medicament for delivery to an airway of a subject, wherein the respiratory medicament delivery device includes a valve that opens responsive to respiratory actuation by the subject; emitting, by a source of ultrasonic energy, ultrasonic energy at an operating frequency such that at least some emitted ultrasonic energy enters the respiratory medicament delivery device; generating, by a sensor output signals conveying information related to one or more characteristics of the ultrasonic energy emitted by the source of ultrasonic energy; determining, based on the generated output signals, a first parameter that indicates energy amplitude of the emitted ultrasonic energy; and detecting one or more flow changes through the valve based on one or more changes of the first parameter, wherein the one or more flow changes are responsive to respiratory actuation by the subject.

It is yet another aspect of one or more embodiments to provide a system configured to deliver medicament to a subject. The system comprises means for combining breathable gas and medicament for delivery to an airway of a subject, wherein the means for combining includes a valve that opens responsive to respiratory actuation by the subject; means for emitting ultrasonic energy such that at least some emitted ultrasonic energy enters the means for combining; means for generating output signals conveying information related to one or more characteristics of the emitted ultrasonic energy; means for determining, based on the generated output signals, a first parameter that indicates energy amplitude of the emitted ultrasonic energy; and means for detecting one or more flow changes through the valve based on one or more changes of the first parameter, wherein the one or more flow changes are responsive to respiratory actuation by the subject.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
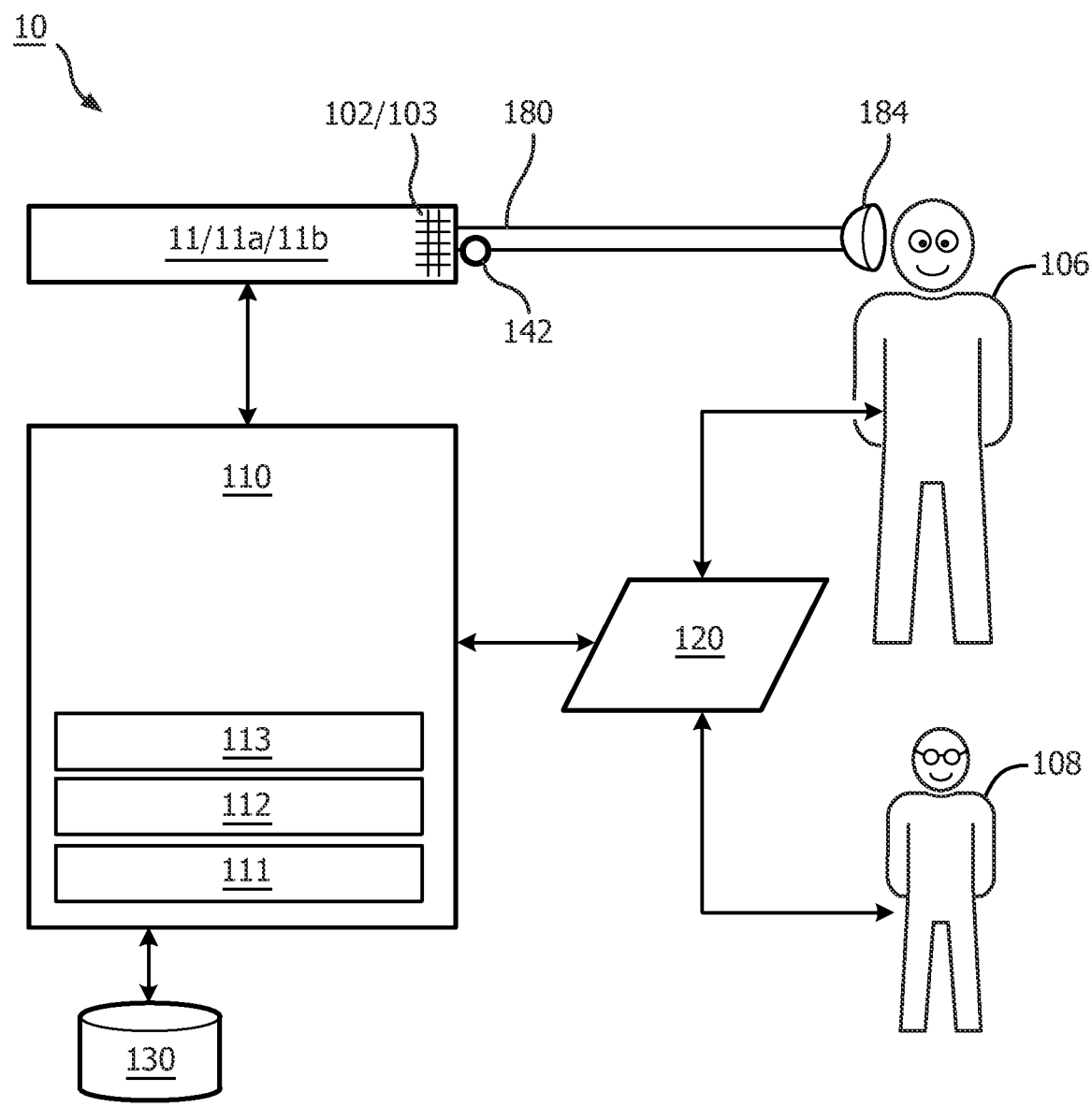
FIG. 1 schematically illustrates a system configured to deliver medicament to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to deliver medicament to a subject 106. System 10 may be included in, integrated in, embedded in, combined with, and/or otherwise operate conjointly with one or more devices including but not limited to devices for respiratory drug delivery, devices that provide oxygen, (positive) airway pressure devices, humidification systems, devices that aid patients with sleeping, devices that provide ventilation and/or other types of respiratory therapy devices. In some implementations, system 10 may include a respiratory medicament delivery device 11. System 10 may include one or more of a source of ultrasonic energy 103, a piezoelectric element 102, one or more sensors 142, one or more processors 110, a parameter determination module 111, a control module 112, a flow module 113, an electronic storage 130, a user interface 120, and/or other components and/or computer program modules.

Respiratory medicament delivery device 11 may include one or more of a jet nebulizer, a mesh nebulizer, an ultrasonic wave nebulizer, a nebulizer 11b, an aerosol generator, a metered-dose inhaler 11a, a dry-powder inhaler, an inhaler, and/or another device configured to deliver medicament to a subject through, at least in part, respiration of the subject. In some implementations, respiratory medicament delivery device 11 may include one or more features of any of these devices. For example, respiratory medicament delivery device 11 may be configured to combine breathable gas, e.g. air, and medicament, e.g. liquid and/or aerosolized drugs, for delivery to the airway of subject 106. In some implementations, respiratory medicament delivery device 11 may be operated by a care provider 108, e.g. a medical professional. In some implementations, the respiratory medicament delivery device 11 may include a conduit 180 to guide gas and/or medicament to subject 106 and/or a mouthpiece or mask 184 to deliver gas and/or medicament from conduit 180 to the airway of subject 106.

Source of ultrasonic energy 103 may be configured to emit ultrasonic energy such that at least some emitted ultrasonic energy enters respiratory medicament delivery device 11. Source of ultrasonic energy 103 may be configured to operate at one or more particular operating frequencies, within one or more particular operating frequency bands, and/or by emitting another type of energy that may be measured by a sensor and/or microphone. In some implementations, including but not limited to nebulizers, source of ultrasonic energy 103 may be an orifice through which compressed air is transferred and/or guided. Such an orifice may be referred to as a leak, although the compressed air may leak intentionally as part of the operation of the respiratory medicament delivery device 11.

In some implementations, respiratory medicament delivery device 11 may emit energy during operation, including, but not limited to, ultrasonic energy. Respiratory medicament delivery device 11 may be configured such that a constituent component thereof displaces air, gas, and/or medicament through mechanical movement at an ultrasonic frequency. In some implementations, respiratory medicament delivery device 11 may be configured such that, responsive to respiratory actuation by a subject, air, gas, and/or medicament is moved into and/or through respiratory medicament delivery device 11 and/or a constituent component thereof. Such displacement may be indirect, e.g. when a moving component is coupled to another component which transfers energy to air and/or gas. In some implementations, respiratory medicament delivery device 11 may emit energy in a frequency range between about 18 kHz and about 200 kHz, between about 15 kHz and about 75 kHz, and/or any sub-range between about 15 kHz and about 200 kHz. The specific frequency range may depend on the type of respiratory medicament delivery device that is used, patient-specific conditions, and/or a range specific to a particular medical condition. In some implementations, emitted and/or measured energy may vary during one or both of inhalation and/or exhalation. Measurements of ultrasonic energy may be used as monitoring and/or diagnostic tools for one or more particular respiratory parameters, (patient) adherence parameters, assessments of patient status and/or health, and/or other characteristic parameters related to respiration. In some implementations, measurements of emitted ultrasonic energy emitted may be used to control breath-activation (interchangeably referred to as breath-actuation) of a respiratory medicament delivery device.

Respiratory medicament delivery device 11 may include a mesh nebulizer and/or components/features thereof. In some implementations, respiratory medicament delivery device 11 may include an ultrasonic wave nebulizer and/or components/features thereof. Respiratory medicament delivery device 11 may include a piezoelectric element 102 to provide mechanical vibration and thus displacement of a medium, e.g. liquid or air. In some implementations, piezoelectric element 102 may be a source of ultrasonic energy 103. In other words, source of ultrasonic energy 103 may be implemented as piezoelectric element 102. Alternatively, and/or simultaneously, source of ultrasonic energy 103 may be separate and distinct from piezoelectric element 102 in some implementations, including but not limited to a jet nebulizer. In some implementations, respiratory medicament delivery device 11 may include an electronic oscillator or similar device/component to control the driving frequency of piezoelectric element 102 and/or another component that is configured for intentional displacement of, e.g., a medium. In some implementations, nebulizers filled with liquid may include moving components that transfer ultrasonic energy to air and/or gas. In some implementations, one or more other surfaces in direct contact with air and/or gas may move as a result of the motion of, e.g., a piezoelectric element or a pump in a portable $O_2$ unit. Any vibrating surface may emit ultrasonic energy. For example, the backside of piezoelectric element 102 may contact (and/or be coupled with) air and/or gas. In some implementations, piezoelectric element 102 is coupled with a mesh (e.g. in a mesh nebulizer) having a side that is directly (or indirectly) in contact with air and/or gas. In some implementations, a static mesh may be placed at some harmonic distance from a vibrating piezoelectric element.

Piezoelectric elements may achieve maximum displacement at one or more particular frequencies, which may be referred to as resonant frequencies. Maximum displacement may be targeted as a preferred mode of operation, at least during medicament delivery. Operating conditions and/or maximum displacement may change over time, e.g. depending on the amount of available medicament within the device, the loading, drift of an oscillator used with/within the device, wear and tear of the device, ambient operating conditions such as temperature, humidity, atmospheric pressure, air density, and/or other factors that may change over time. Operating conditions and/or maximum displacement may differ between individual devices, e.g. based on construction, assembly, and/or other device-specific conditions. The particular operating condition having maximum displacement may be assumed to coincide, or at least be close to, the operating condition in which a maximum amount of ultrasonic energy is emitted. As used herein, the term "maximum" may refer to a local maximum in a specific range of operation.

By virtue of this disclosure, operating conditions for respiratory medicament delivery devices may be controlled and/or adjusted to track changes in measurements of ultrasonic energy. Alternatively, and/or simultaneously, (patient-specific) respiratory parameters and/or adherence parameters (e.g. as indicated through device usage information and/or device actuation information) may be monitored through measurements of ultrasonic energy. In some implementations, adjustments may be made in real-time or near-real-time. In some implementations, adjustments may be made automatically, autonomously, and/or without (manual) user intervention.

Figure 12:
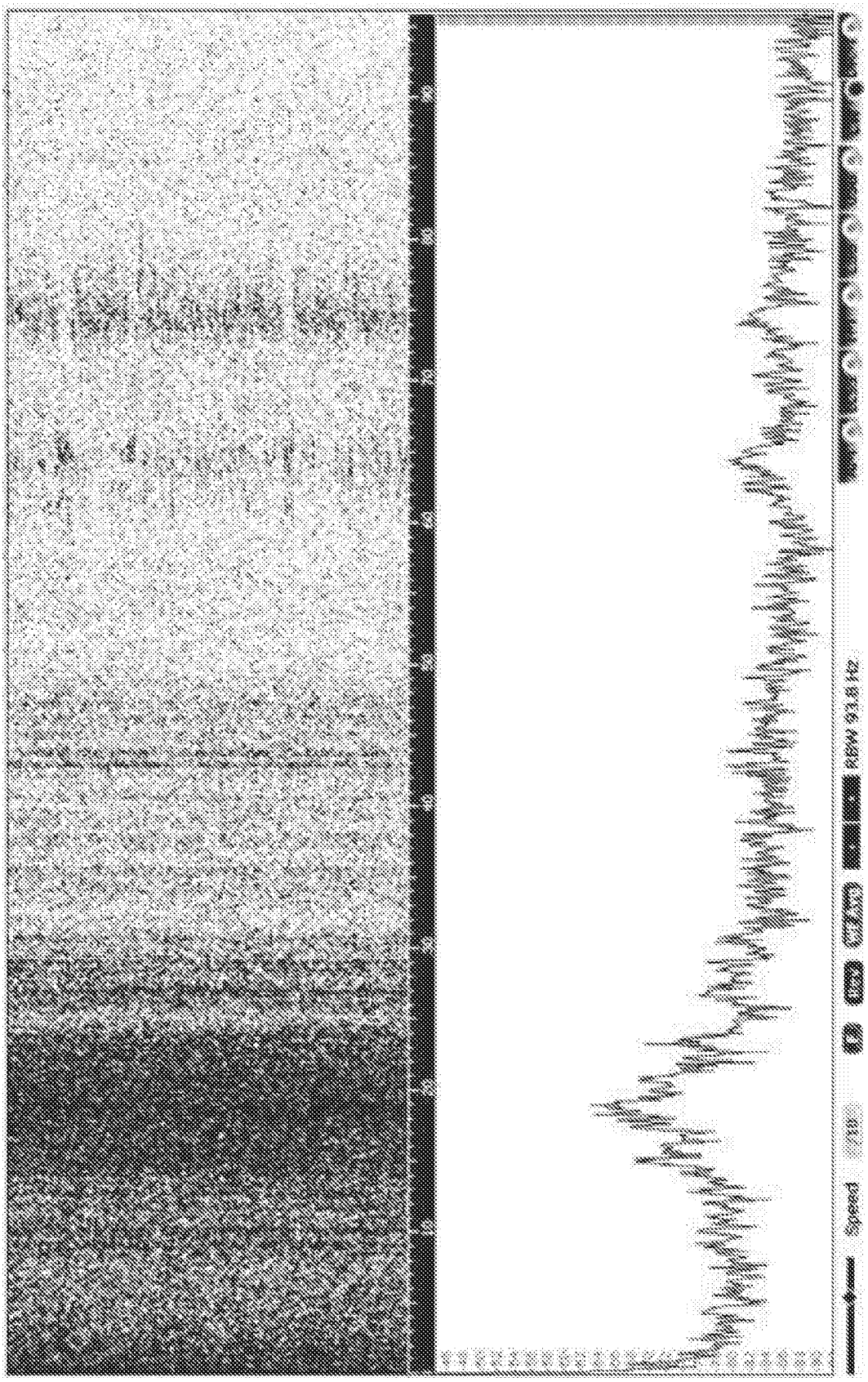
FIGS. 12, 13, and 14 illustrate graphs for energy emitted during the operation of various respiratory medicament delivery devices.
Figure 13:
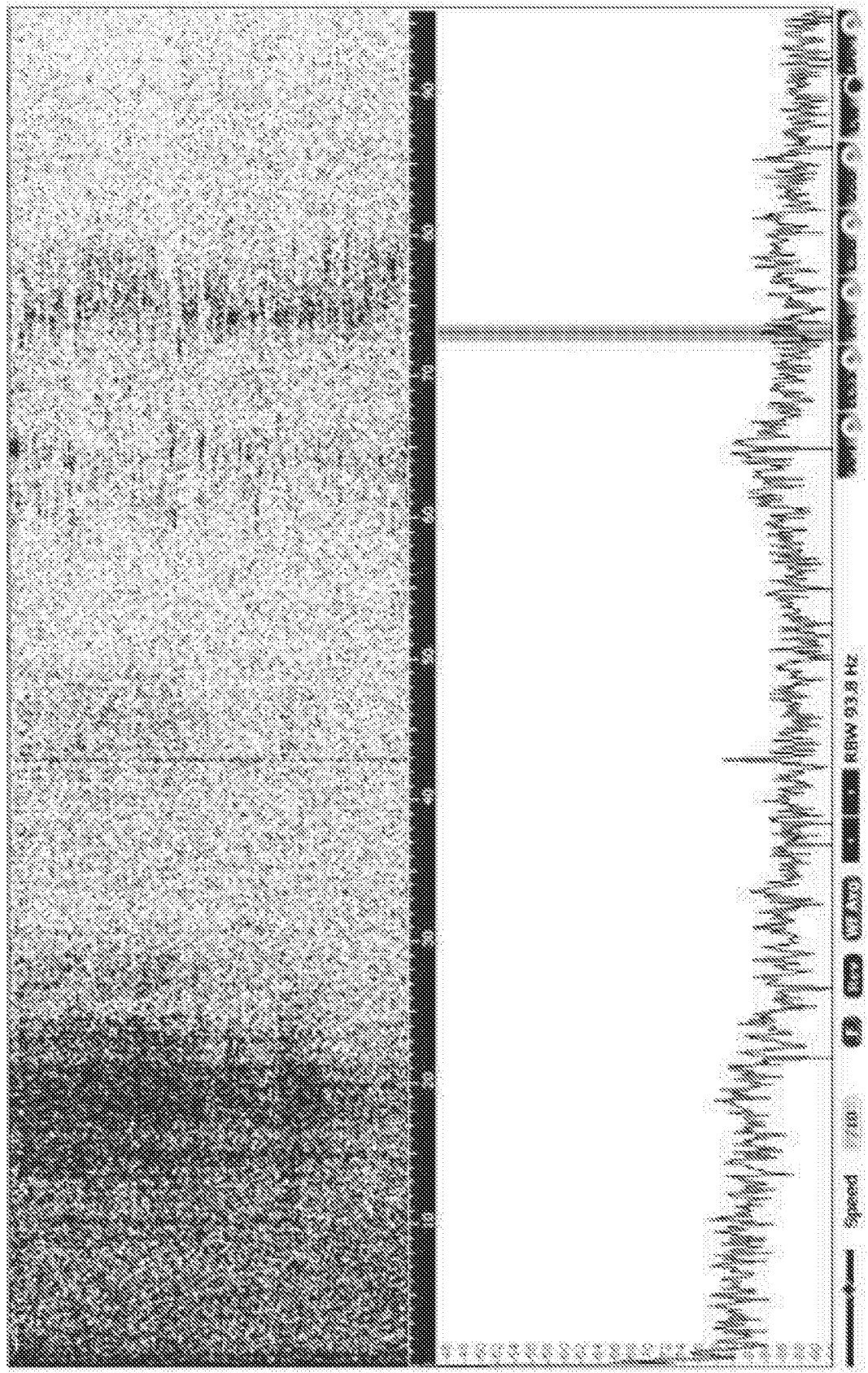

By way of illustration, FIG. 12 illustrates a graph 1200 for energy emitted during the operation of a jet nebulizer. Graph 1200 includes a waterfall display in the top half, and a magnitude (of energy amplitude) in the bottom half. The waterfall display shows time on the vertical axis and measured frequency (in kHz) on the horizontal axis. As depicted in FIG. 12, graph 1200 includes a peak magnitude 1201 at a frequency of about 15 to 21 kHz. Additional local peaks 1202 and 1203 are noticeable at frequencies of about 64 and 74 kHz, respectively, which may be related to the nebulization process. Referring to FIG. 1, energy may be measured using one or more sensors 142. As used herein, the term "magnitude" may be used to refer to the energy amplitude at a particular frequency and/or within a particular range of frequencies. By way of further illustration, FIG. 13 illustrates a graph 1300 captured at the commencement of sputter for the same jet nebulizer as described in relation to FIG. 12. The amount of energy measured at frequencies of about 15 to 21 kHz, 64 kHz, 74 kHz, and/or other frequencies differs between graph 1200 of FIG. 12 and graph 13 of FIG. 13.

One or more sensors 142 of system 10 in FIG. 1 are configured to generate output signals representing one or more characteristics of ultrasonic energy emitted by one or more sources of ultrasonic energy 103. In some implementations, sensor 142 may include a microphone (interchangeably referred to as microphone 142). For example, sensor 142 may include a microphone constructed as a micro-electro-mechanical system (MEMS) or nano-electro-mechanical system (NEMS). As used herein, the term "MEMS" may be used to refer to either MEMS or NEMS. As used in this disclosure, the term "microphone" may be used to refer to a MEMS microphone, and may be used for audible and/or ultrasonic frequencies/sounds from any source or sources that emit such energy, including subject 106.

The one or more sensors 142 may include an accelerometer, positional sensor, movement sensor, light sensor, infrared (IR) sensor, electromagnetic sensor, electrode, tilt meter, (video) camera, and/or other sensors. The illustration of sensor 142 including one member in FIG. 1 is not intended to be limiting. In some embodiments, system 10 may use multiple sensors. The illustration of the location of sensor 142 as depicted in FIG. 1 is not intended to be limiting. An individual sensor 142 may be located at or near (a body part of) subject 106, embedded and/or integrated in a respiratory device, and/or at other locations. Resulting output signals or conveyed information from one or more sensors 142 may be transmitted to processor 110, user interface 120, electronic storage 130, and/or other components of system 10. Transmission may be wired and/or wireless.

The one or more sensors 142 may be configured to generate output signals in an ongoing manner, e.g. before, during, and/or after delivery of medicament. This may include generating signals intermittently, periodically (e.g. at a sampling rate), continuously, continually, at varying intervals, and/or in other ways that are ongoing. The sampling rate may be about $10^{-9}$ second, about $10^{-8}$ second, about $10^{-7}$ second, $10^{-6}$ second, $10^{-5}$ second, $10^{-4}$ second, $10^{-3}$ second, 0.01 second, 0.1 second, 1 second, about 10 seconds, about 1 minute, and/or other sampling rates. It is noted that multiple individual sensors 142 may operate using different sampling rates, as appropriate for the particular output signals and/or (frequencies related to particular) parameters and/or characteristics derived therefrom. For example, in some embodiments, the generated output signals may be considered as a vector of output signals, such that a vector includes multiple samples of information conveyed related to one or more parameters and/or characteristics. A particular parameter or characteristic determined in an ongoing manner from a vector of output signals may be considered as a vector of that particular parameter or characteristic.

In some implementations, sensor 142 may include a MEMS microphone configured and/or arranged to measure ultrasonic energy transferred from any flat and/or curved surface within a respiratory device, any exterior surface thereof, and/or (the airway of) subject 106. For example, measured (ultrasonic) energy may be different between inhalation and exhalation. During inhalation, subjects may emit ultrasonic energy having a frequency of about 20 kHz. During exhalation, subjects typically emit ultrasonic energy having a frequency lower than 20 kHz, or no discernible emission of ultrasonic energy. This distinction between inhalation and exhalation may be used by the systems and methods described herein.

In some implementations, sensor 142 may be configured to generate output signals conveying measurements related to gas parameters of respiratory airflow, parameters related to airway mechanics, and/or other parameters. Gas parameters may include flow, flow rate, strength of inhalation by a patient, (airway) pressure, humidity, velocity, acceleration, and/or other gas parameters, as well as derivatives thereof. Output signals may convey measurements related to respiratory parameters, including but not limited to respiratory timing and respiratory rate. Respiratory timing may include one or more of onset of inhalation, duration of inhalation, onset of respiratory pause between inhalation and exhalation, duration of respiratory pause, onset of exhalation, duration of exhalation, respiratory rate, inhalation-to-exhalation ratio (I:E ratio), device usage information, and/or other timing characteristics related to respiration. Sensor 142 may be in fluid communication with conduit 180 and/or mouthpiece or mask 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject.

Figure 3:
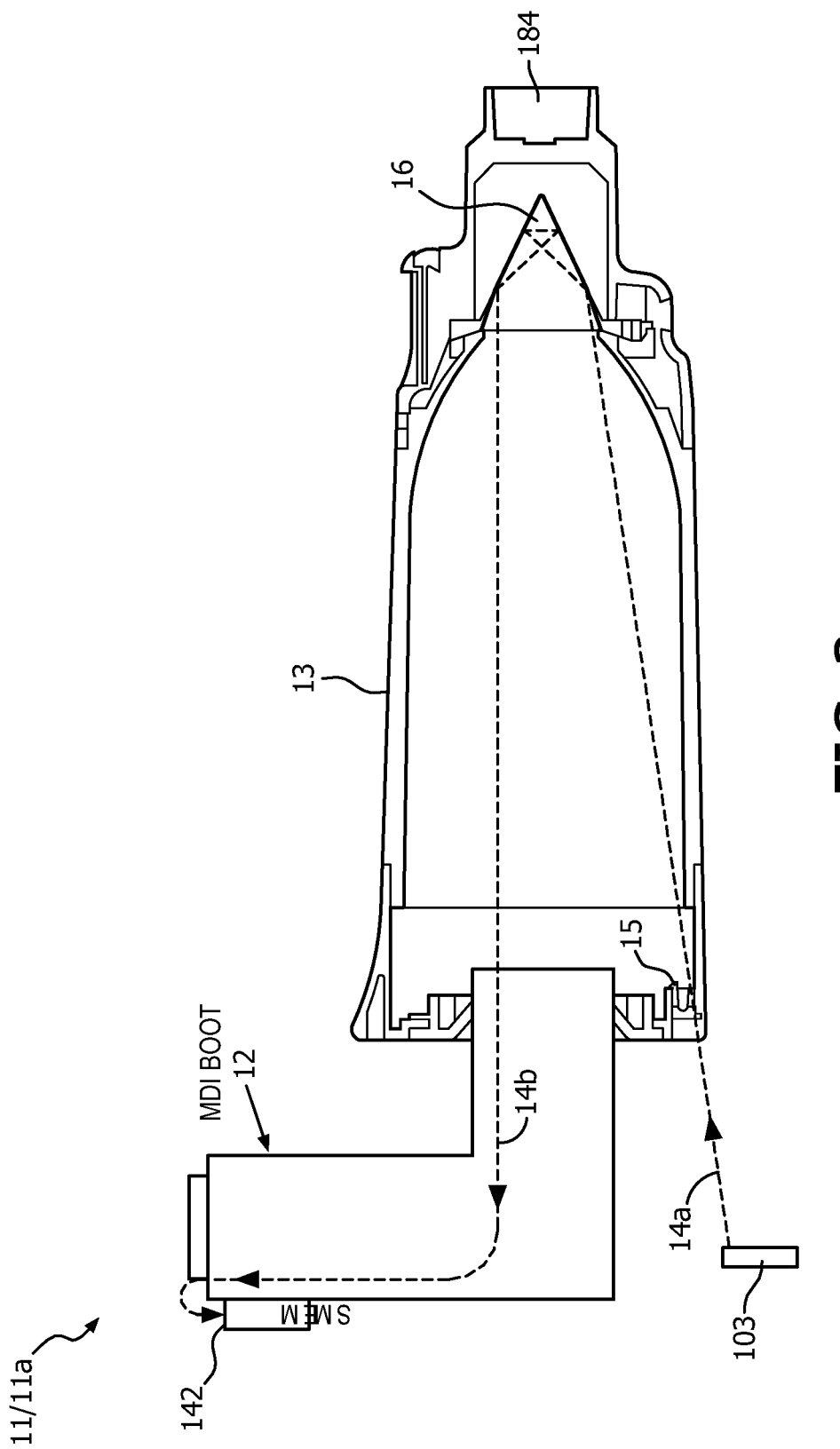
FIGS. 3 and 4 illustrate a metered-dose inhaler (MDI) that includes a valved holding chamber and a duck-bill valve.

Referring to FIG. 3, in some implementations, respiratory medicament delivery device 11 may include an inhaler 11a with a valved holding chamber 13 (VHC) and a valve 16 (e.g. an inhalation valve or a duckbill valve) in fluid coupling with subject interface appliance 184 (e.g. a mouthpiece). By way of non-limiting example, inhaler 11a may be a metered-dose inhaler (MDI) 11a that includes an MDI boot 12. The emitted ultrasonic energy for meter-dose inhalers may be a (brief) wide-band signal between about 15 kHz and 25 kHz. Source of ultrasonic energy 103 may be configured to emit ultrasonic energy along a potential path 14a (which is exemplary and not intended to be limiting) through an opening 15 (interchangeably referred to as a port or sound reed port) of the valved holding chamber 13. By way of illustration, source of ultrasonic energy 103 may include one or more of a sound emitter, an air-transducer, and/or other source of ultrasonic energy. The emitted energy may be at a frequency of about 28 kHz, about 40 kHz, about 128 kHz, and/or another frequency in the range between 15 kHz and 200 kHz. By way of illustration, opening 15 may include a sound reed. Emitted sound may enter valved holding chamber 13, valve 16, MDI boot 12, and/or other components of respiratory medicament delivery device 11 (e.g. metered-dose inhaler 11a as depicted in FIG. 3). Along a path 14b (which is exemplary and not intended to be limiting), emitted ultrasonic energy may be guided to and/or measured through microphone 142. Note that the placement of microphone 142 as depicted is merely exemplary and not intended to be limiting in any way. For example, in some implementations, microphone 142 may be integrated within valved holding chamber 13.

In some implementations, a constant and/or prolonged emission of ultrasonic energy into respiratory medicament delivery device 11 (e.g. into valved holding chamber 13) may produce a stable pattern of mixed waves of ultrasonic energy, e.g. bouncing around within respiratory medicament delivery device 11. A constant and/or consistent signal may thus be generated by microphone 142. Responsive to respiratory actuation (e.g. a subject breathing in through subject interface appliance 184) valve 16 may open, albeit briefly. The opening of valve 16 may alter the geometry within respiratory medicament delivery device 11 (in particular within valved holding chamber 13) such that the emitted ultrasonic energy along path 14a, path 14b, and/or forming a particular pattern may change, thus changing the signal generated by microphone 142. By way of non-limiting example, signal changes may include one or more of phase changes, changes in magnitude, and/or other changes. Increased flow through valve 16 may increasingly open valve 16 wider (e.g. move one or more flaps of a duck-bill valve) and in a predetermined manner alter the signal generated by microphone 142. This signal may correspond to the flow through valve 16.

Figure 4:
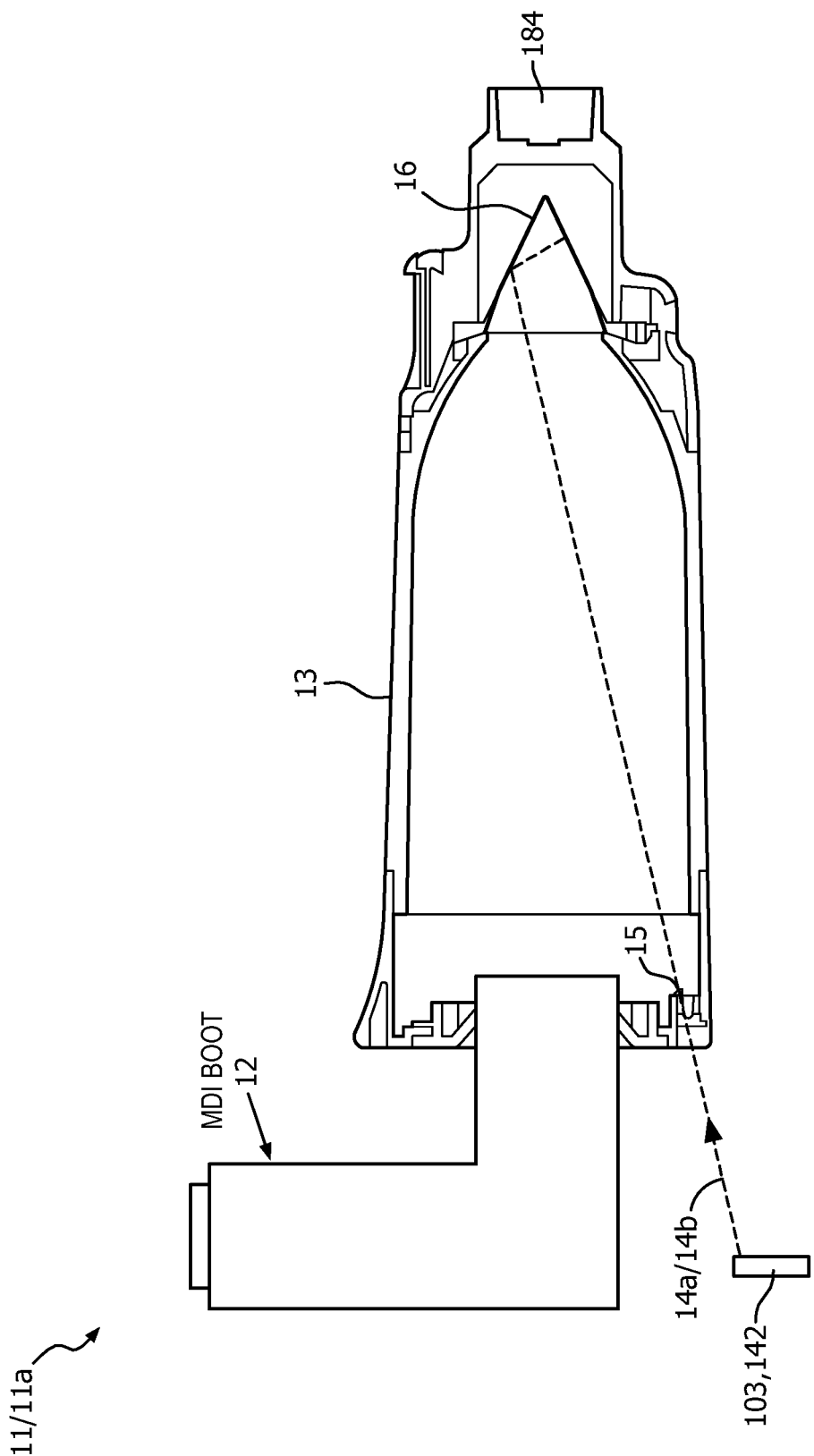

By way of further illustration, FIG. 4 illustrates a respiratory medicament delivery device 11 similar to the depiction in FIG. 3. In FIG. 4, ultrasonic energy from source of ultrasonic energy 103 is angled, aimed, and/or directed through opening 15 in such a way that path 14a and path 14b may both go through opening 15. In such a case, a microphone (and/or, as depicted, a transducer acoustic interferometer 142) may be placed at or near opening 15 to generated output signals conveying information related to one or more characteristics of the ultrasonic energy within respiratory medicament delivery device 11. In some implementations, the source of ultrasonic energy and the sensor may be embedded and/or combined in the same device (e.g. labeled both as 103 and 142 in FIG. 4).

Figure 10:
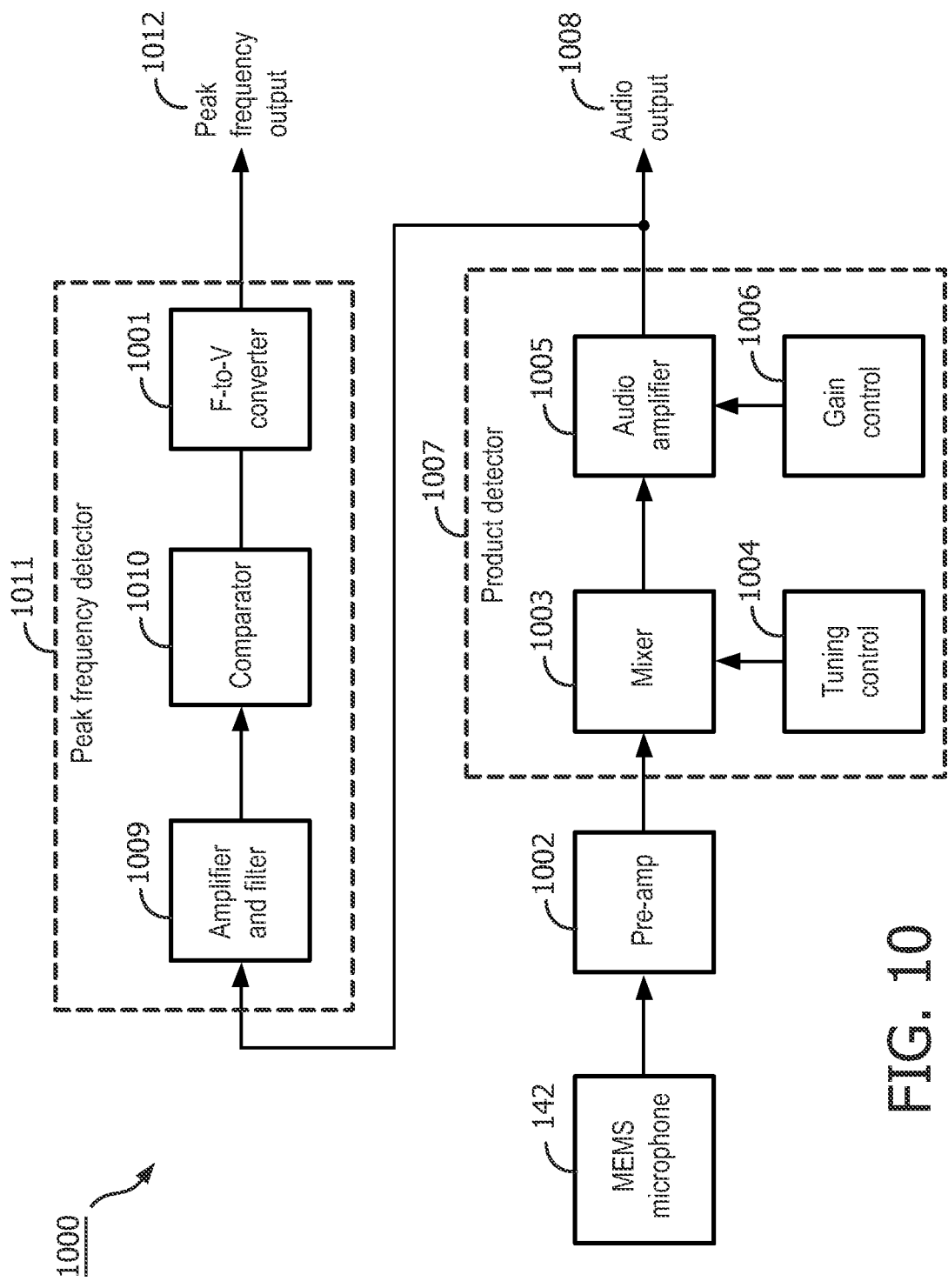
FIGS. 10 and 11 illustrate subsystems for processing signals representing received ultrasonic energy as may be used in a system configured to deliver medicament to a subject.
Figure 11:
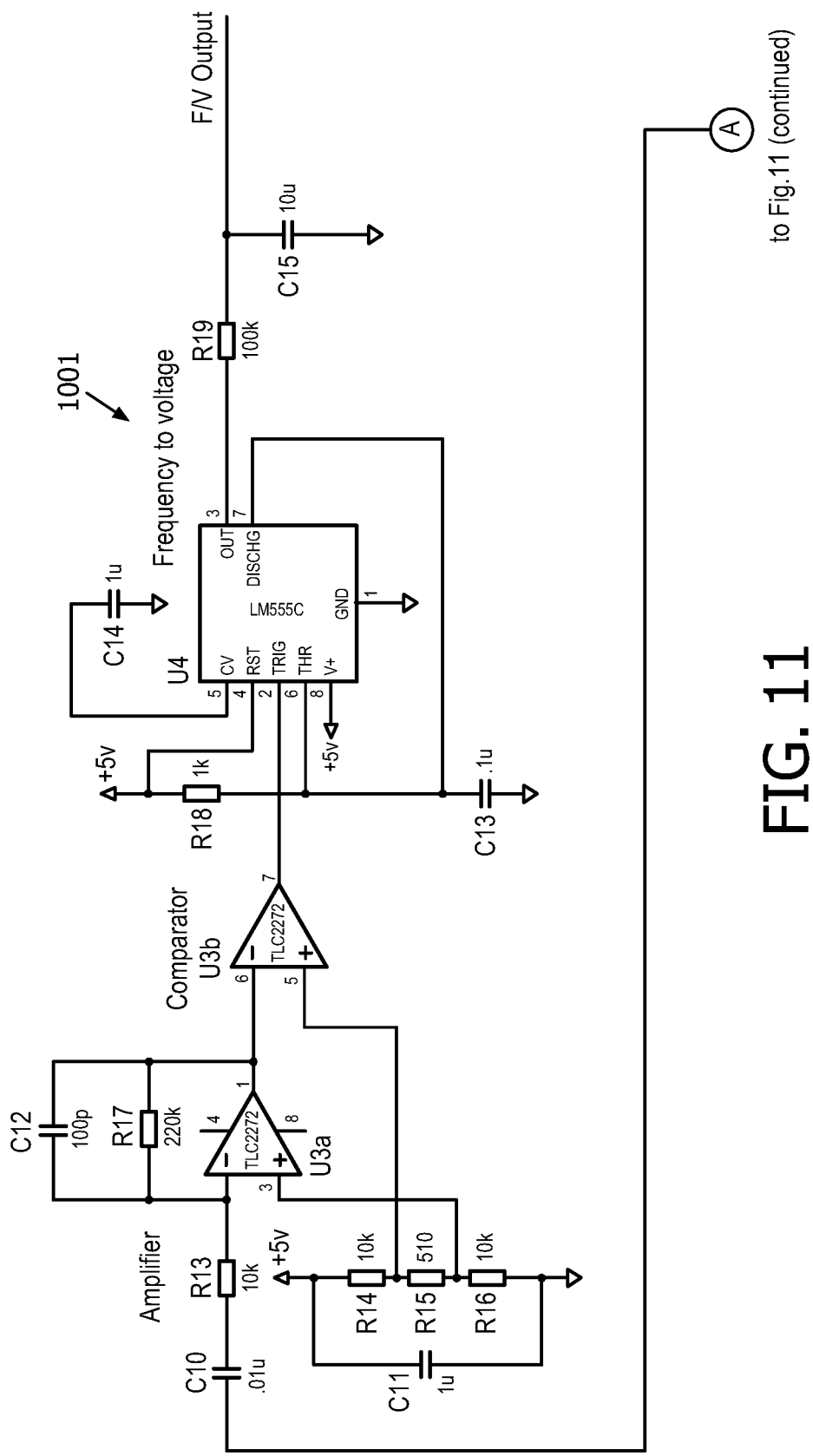
Figure 11:
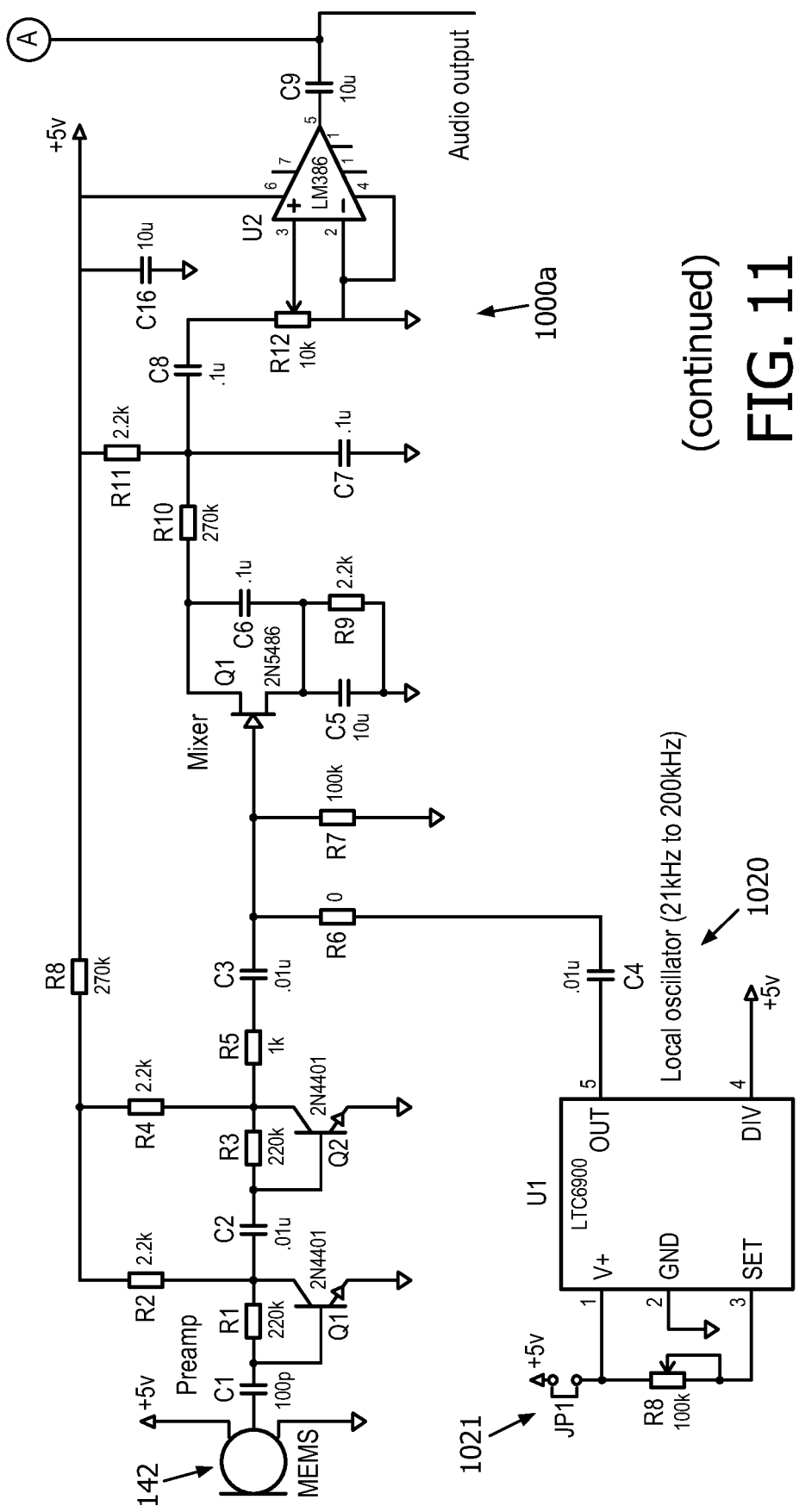

FIGS. 10 and 11 schematically illustrate various components forming subsystems 1000 and 1000a, respectively. Subsystems 1000 and 1000a may include a frequency-to-voltage circuit 1001. Subsystems 1000 and 1000a may represent similar features and functionality. Subsystem 1000, subsystem 1000a, and/or components thereof may be included and/or used in embodiments of system 10 (FIG. 1). Acoustic and/or ultrasonic energy may be received and/or measured by microphone 142. A pre-amplifier 1002 may be configured to include a high pass filter and/or a coupling capacitor. Depending on the application, the coupling capacitor may range from about 100 pf (for short range measurements within about a 1 foot distance) to about 5600 pf (for longer range measurements between about 1 foot and about 10 feet distance). Pre-amplifier 1002 may be used before the incoming signal is amplified, for example as depicted in FIG. 11 by using two transistors. A product detector 1007 may be configured to detect the type of respiratory medicament delivery device in operation, based on the measured ultrasonic energy. Product detector 1007 may include mixer 1003, tuning control 1004, audio amplifier 1005, gain control 1006, and/or other components. Mixer 1003 may include a transistor driven by both pre-amplifier 1002 and (as depicted in FIG. 11) a local oscillator 1020. Mixer 1003 may be configured to multiply its two inputs with the resulting output, thus producing sum and difference frequencies. Audio amplifier 1005 may be configured to amplify the signal created by mixer 1003 and/or to provide a comfortable listening level for a user listening to audio output 1008. Gain control may be configured to control gain for audio amplifier 1005. Output from audio amplifier 1005 may be transmitted to peak frequency detector 1011. Peak frequency detector 1011 may include an amp-and-filter 1009, a comparator 1010, a frequency-to-voltage circuit 1001, and/or other components. Peak frequency detector 1011 may be configured to generate a (direct current) output voltage that is proportional to the (dominant) frequency as received through microphone 142. Amp-and-filter 1009 may provide additional amplification and filtering of the signal prior to comparator 1010 digitizing it. The resulting pulse train may be used to trigger a pulse entering a capacitor, thus adding charge to the capacitor. The charge on the capacitor may represent the (dominant) frequency as received through microphone 142. Alternatively, and/or simultaneously, such a pulse train may be used to increment a timer and/or counter, to provide similar utility as the capacitor.

In some implementations, subsystems the same as or similar to subsystems 1000 and 1000a may be used as narrow-band special-purpose microphones. For example, the emitted ultrasonic energy for mesh nebulizers and dry-powder inhalers may be a narrow-band signal for which subsystems 1000 and 1000a as depicted may be suitable.

Figure 5:
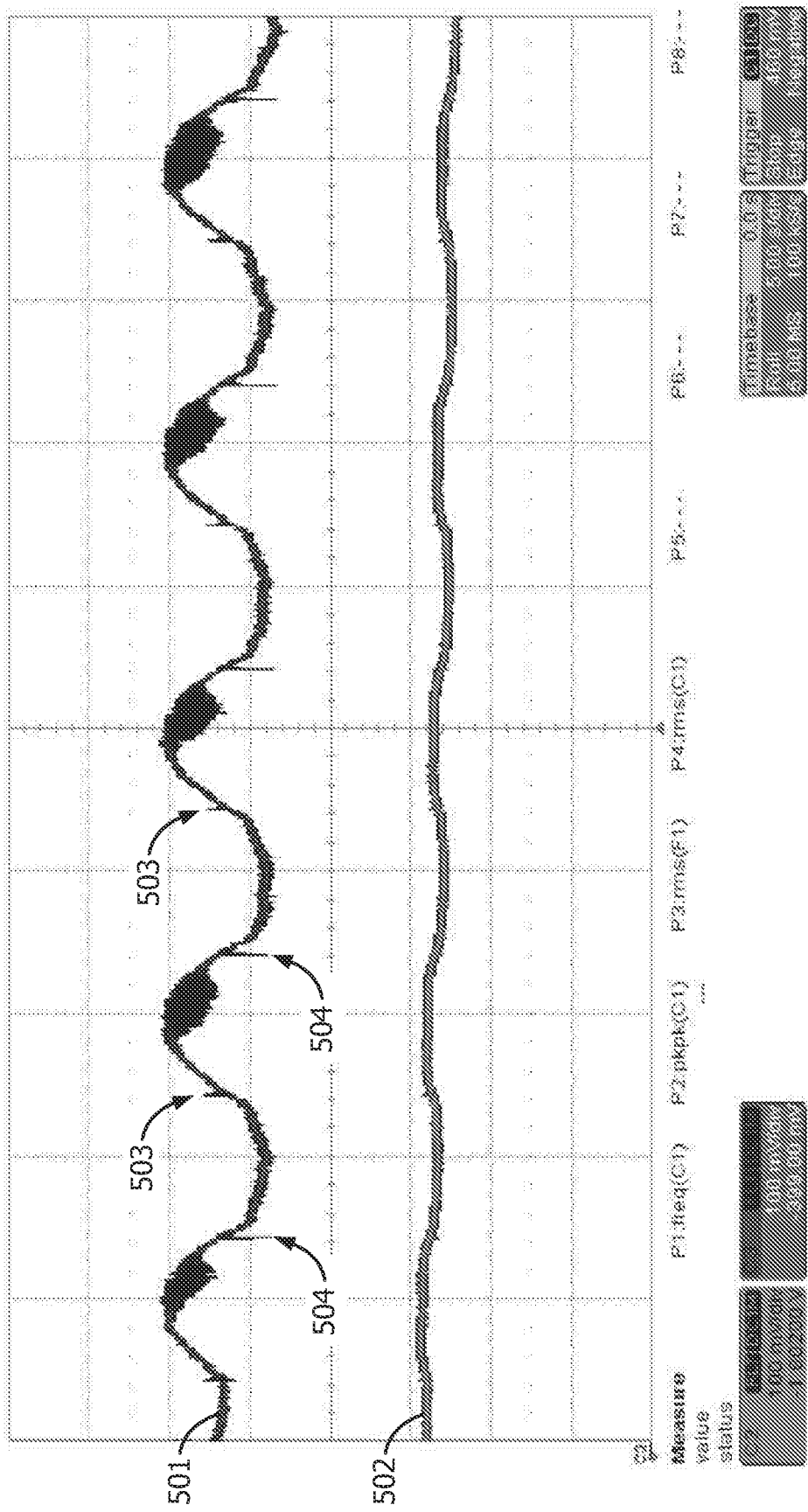
FIGS. 5, 6, 7, 15, and 16 illustrate voltage signals as may be produced by a system configured to deliver medicament, the voltage signals corresponding to measured ultrasonic energy.
Figure 6:
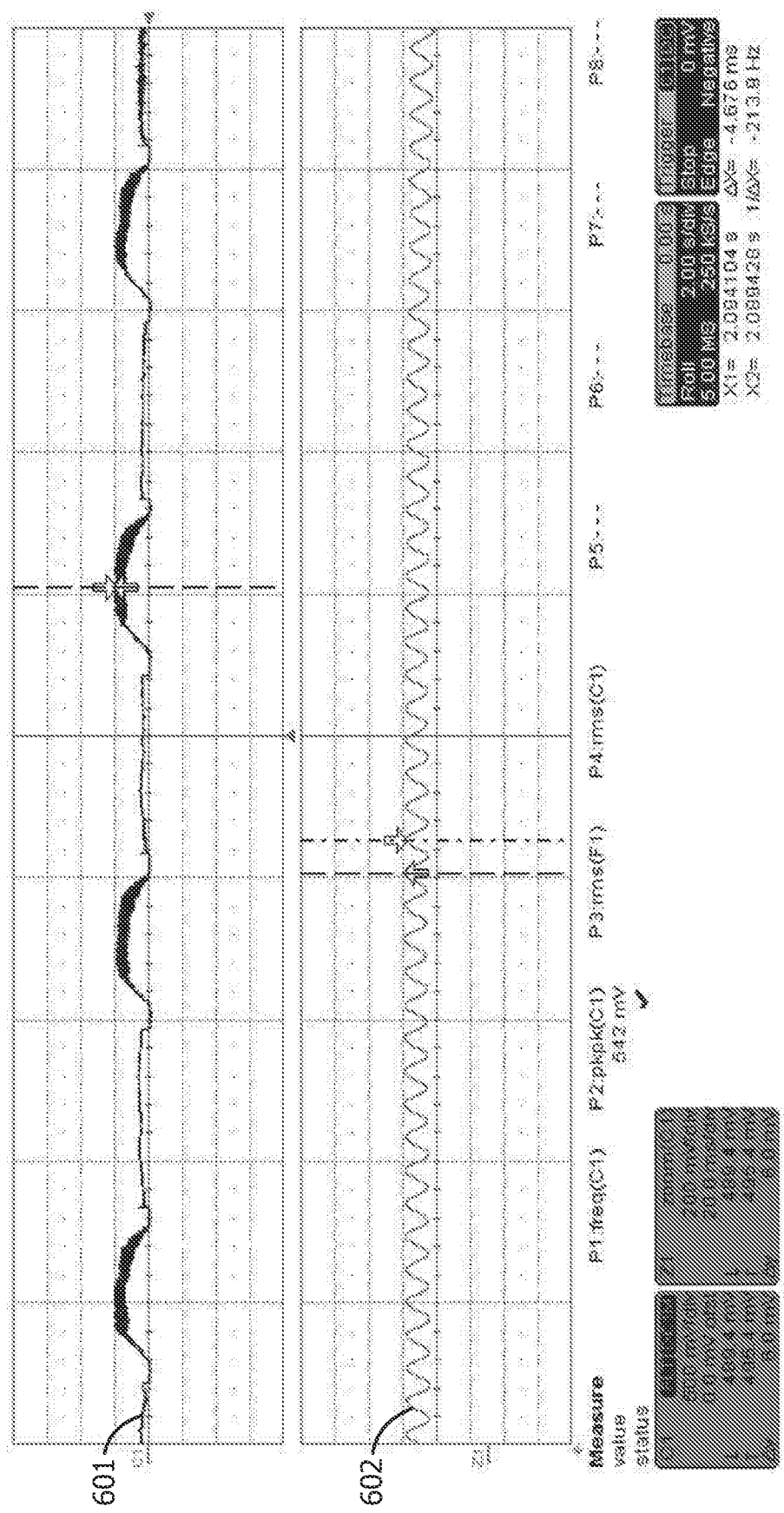
Figure 7:
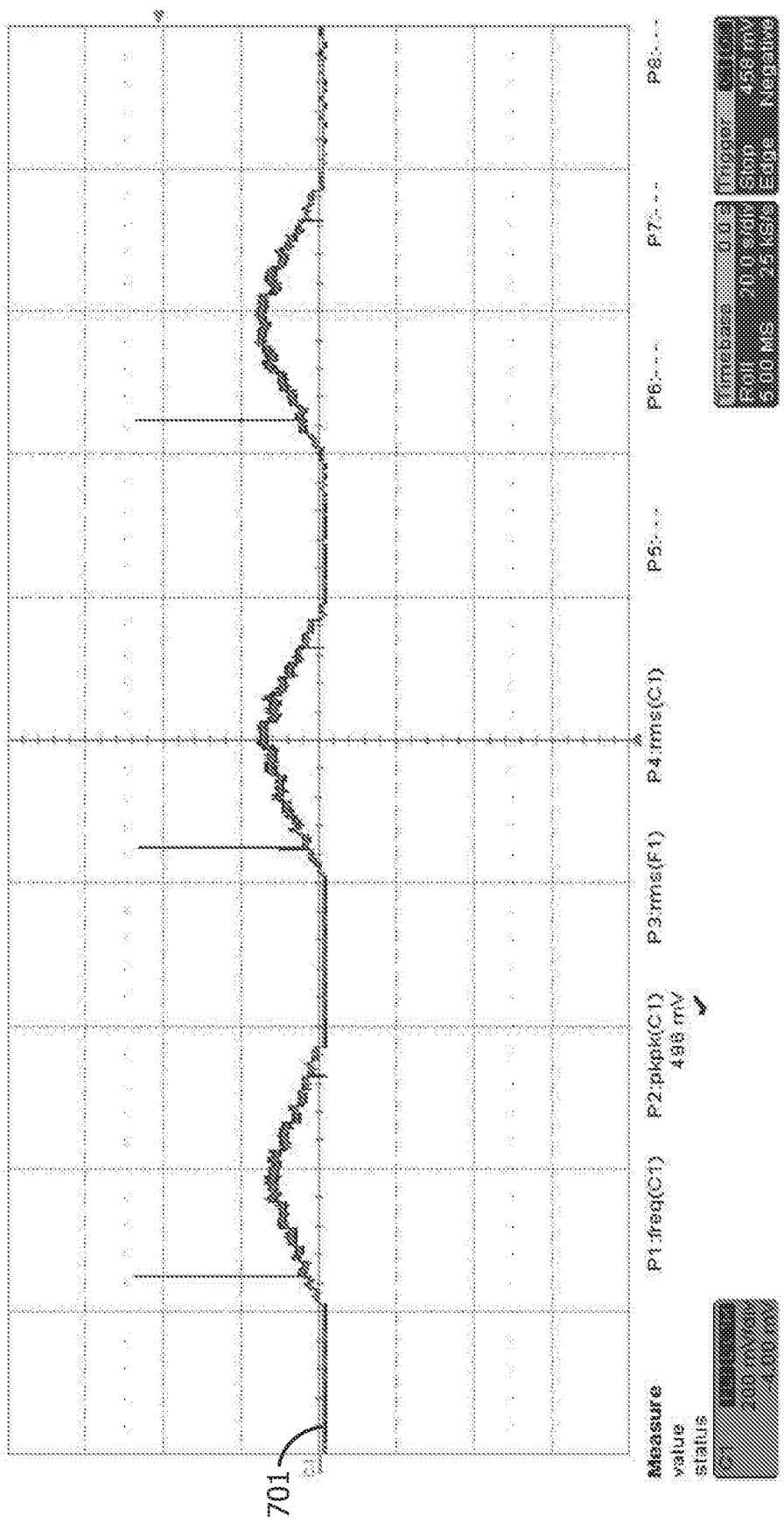

By way of illustration, FIGS. 5, 6, and 7 illustrates graphs 500, 600, and 700 for energy emitted during operation of a respiratory medicament delivery device 11 such as depicted in FIGS. 3 and 4. FIG. 5 illustrates graph 500 depicting voltage signals 501 and 502 as may be produced by subsystem the same as or similar to subsystem 1000 and 1000a (as described elsewhere herein in relation to FIGS. 10 and 11), through frequency-to-voltage circuit 1001 (FIG. 10). Voltage signals 501 and 502 may be produced by measuring ultrasonic energy emitted by a source of ultrasonic energy operating at a frequency of about 40 kHz, using a simulated breathing rate of 6 BPM and a breath volume of 400 mL drawn through a valve of a valved holding chamber (similar to respiratory medicament delivery device 11 depicted in FIGS. 3 and 4). Signal 501 reflects a signal based on a signal generated by a microphone. Signal 502 reflects the signal measured through an acoustic interferometer. Positive slopes and/or spikes 503 in signal 501 correspond to the beginning of inhalations. Negative slopes and/or spikes 504 correspond to the beginning of exhalations. The oscillation near the peaks of signal 501 may correspond to oscillations of the (duck-bill) valve under low flow conditions. Signal 501 and signal 502 may be synchronized to the respiratory actuation.

FIG. 6 illustrates graph 600 depicting voltage signals 601 and 602 as may be produced by subsystem the same as or similar to subsystem 1000 and 1000a (as described elsewhere herein in relation to FIGS. 10 and 11), through frequency-to-voltage circuit 1001 (FIG. 10). Voltage signals 601 and 602 may be produced by measuring ultrasonic energy emitted by a source of ultrasonic energy operating at a frequency of about 40 kHz, using a simulated breathing rate of 6 BPM and a breath volume of 400 mL drawn through a valve of a valved holding chamber (similar to respiratory medicament delivery device 11 depicted in FIGS. 3 and 4). Signal 601 reflects a signal based on a signal generated by a microphone. Signal 602 reflects a magnified view of signal 601 that illustrates the oscillations. The oscillations near the peaks of signal 601 apparently correspond to a frequency of about 214 Hz, which may reflect oscillation of the duck-bill valve at low flow conditions.

FIG. 7 illustrates graph 700 depicting voltage signal 701 as may be produced by subsystem the same as or similar to subsystem 1000 and 1000a (as described elsewhere herein in relation to FIGS. 10 and 11), through frequency-to-voltage circuit 1001 (FIG. 10). Voltage signals 702 may be produced by measuring ultrasonic energy emitted by a source of ultrasonic energy operating at a frequency of about 40 kHz, using a simulated breathing rate of 1 BPM and a breath volume of 100 mL drawn through a valve of a valved holding chamber (similar to respiratory medicament delivery device 11 depicted in FIGS. 3 and 4). Signal 701 reflects a signal based on a signal generated by a microphone over a period of about 3 minutes, depicting 3 breaths. The detected flow is well below flows considered possible for patients, which illustrates the sensitivity of this approach for monitoring respiratory medicament delivery devices. Alternatively, and/or simultaneously, changes within respiratory medicament delivery device 11, including but not limited to operating conditions such as temperature, humidity, atmospheric pressure, air density and/or chemical composition of a gas (including but not limited to the percentage of $CO_2$ in a particular volume of gas) may be measurable in the manner described in this disclosure. Information derived from graphs such as graphs 500, 600, and 700 may be used to control operation of a respiratory medicament delivery device and/or monitor respiratory parameters (e.g. as indicative of patient adherence).

Referring to FIG. 1, in some implementations, respiratory medicament delivery device 11 may include a nebulizer (e.g. a jet nebulizer) and/or components/features thereof. Jet nebulizers may include compressed air. The emitted ultrasonic energy for some types of respiratory medicament delivery devices, including but not limited to nebulizers, may be a wide-band signal. Such a signal may be measured using a subsystem such as subsystem 1000a in FIG. 11, but with jumper 1021 removed (and resistor R9 changed from 10 kOhm to 2 kOhm), and thereby not using product detector 1007 (as depicted in FIG. 10) or local oscillator 1020 (as depicted in FIG. 11). In this mode of operation, the subsystem may be suitable for monitoring wide-band signals between about 15 kHz and about 65 kHz.

Figure 8:
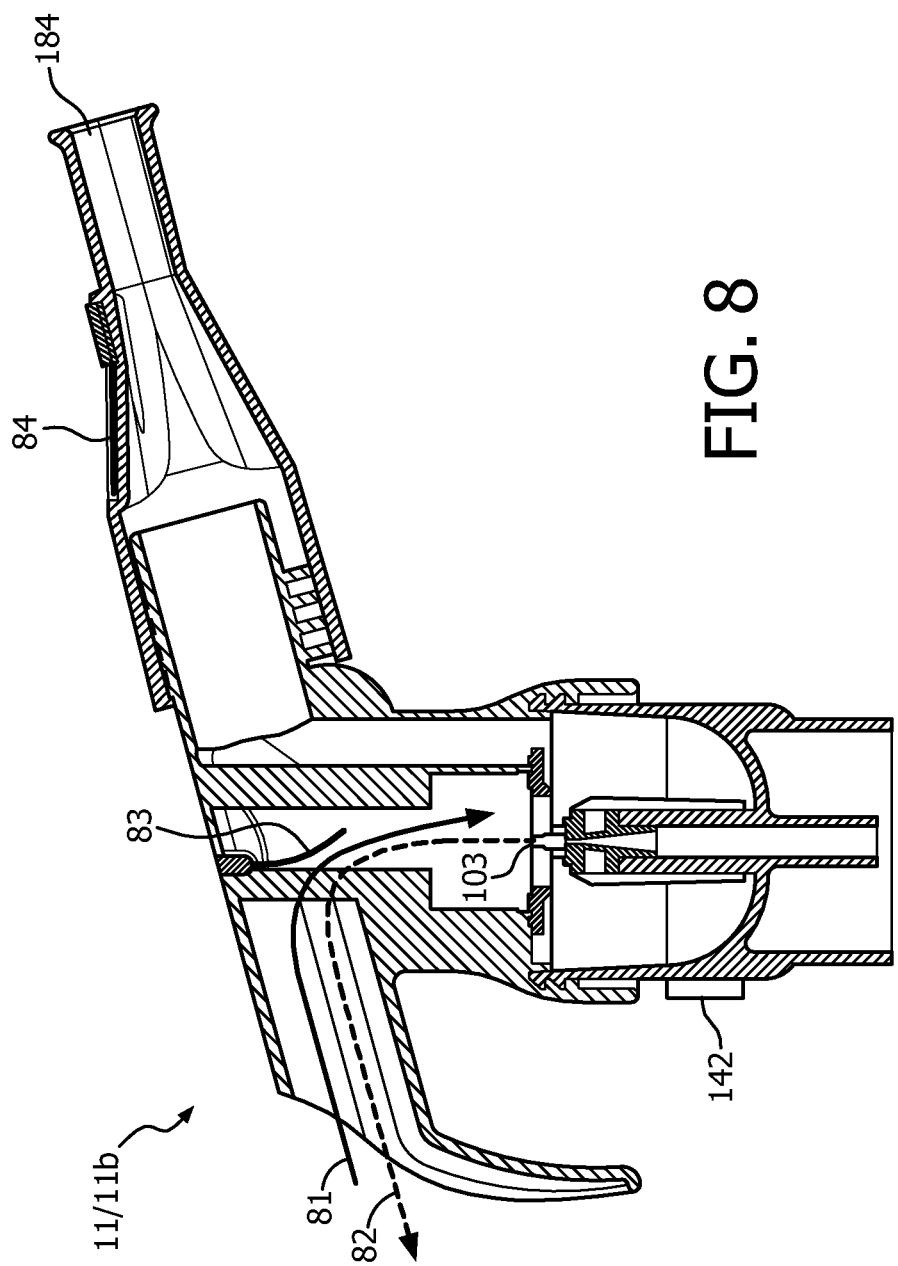
FIGS. 8 and 9 illustrate an nebulizer that includes a separate inhalation valve and exhalation valve.
Figure 9:
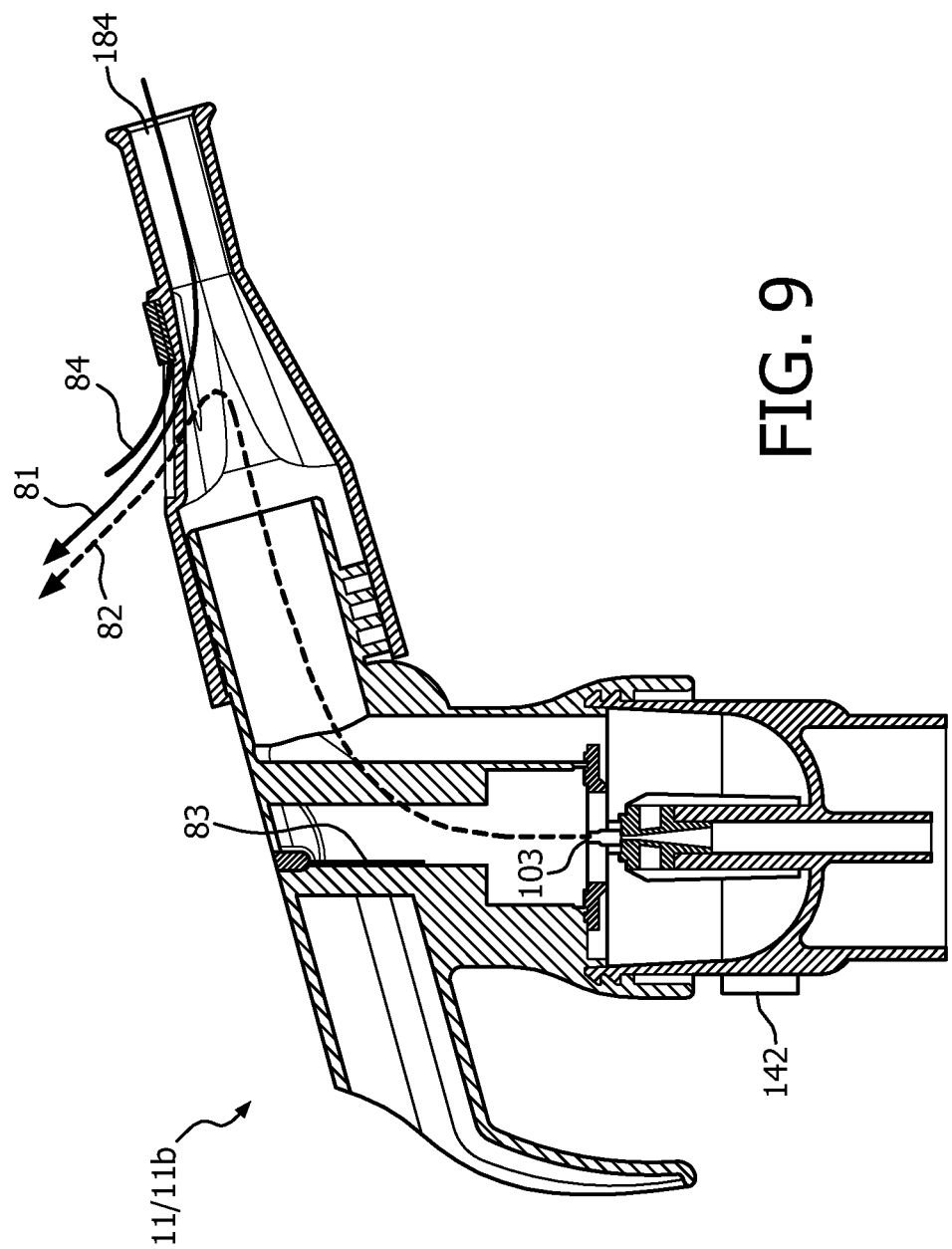

By way of illustration, FIGS. 8 and 9 illustrate a respiratory medicament delivery device 11 that includes a (breath-enhanced) nebulizer 11b that operates through a combination of (flap) valves, in this case an inhalation valve 83 and, separately, an exhalation valve 84. During inhalation, as depicted in FIG. 8, air and/or breathable gas enters, according to direction 81, through inhalation valve 83 into respiratory medicament delivery device 11. At the same time, ultrasonic energy (generated within nebulizer 11b as compressed air passes through a small orifice, which functions as source of ultrasonic energy 103) is emitted from nebulizer 11b, according to direction 82, through inhalation valve 83. The position of microphone 142 on the left side of the nebulizer as depicted is not intended to be limiting in any way. In some implementations, a respiratory medicament delivery device 11 may include more than one microphone 142, e.g. two microphones positioned on opposite sides of the nebulizer, positioned at or near one or more valves, and/or at other positions that are appropriate to measure emitted ultrasonic energy from respiratory medicament delivery device 11.

During exhalation, as depicted in FIG. 9, air and/or breathable gas is exhaled through valve 84, according to direction 81, e.g. into the ambient atmosphere. At the same time, ultrasonic energy (generated within nebulizer 11b) is emitted from nebulizer 11b, according to direction 82, through exhalation valve 84. By placing one or more microphones 142 in sufficient proximity to the directions as indicated by direction 82 in FIGS. 8 and 9, and by virtue of this disclosure, a system that includes a respiratory medicament delivery device such as nebulizer 11b may be configured to measure and/or monitor respiratory parameters, respiratory timing, device usage information (including but not limited to usage time by a patient, average treatment time, time directly on the nebulizer, amount of drug delivered, number of drug delivery sessions in a day or week, and/or other device usage information), and/or other information. For example, by combining device actuation information with one or more respiratory parameters and/or the recommended treatment for a subject, one or more patient adherence metrics may be determined. Alternatively, and/or simultaneously, a breath-actuated mode of operation may be enabled by virtue of this disclosure. Combination of different types of derived information is contemplated within the scope of this disclosure.

Figure 14:
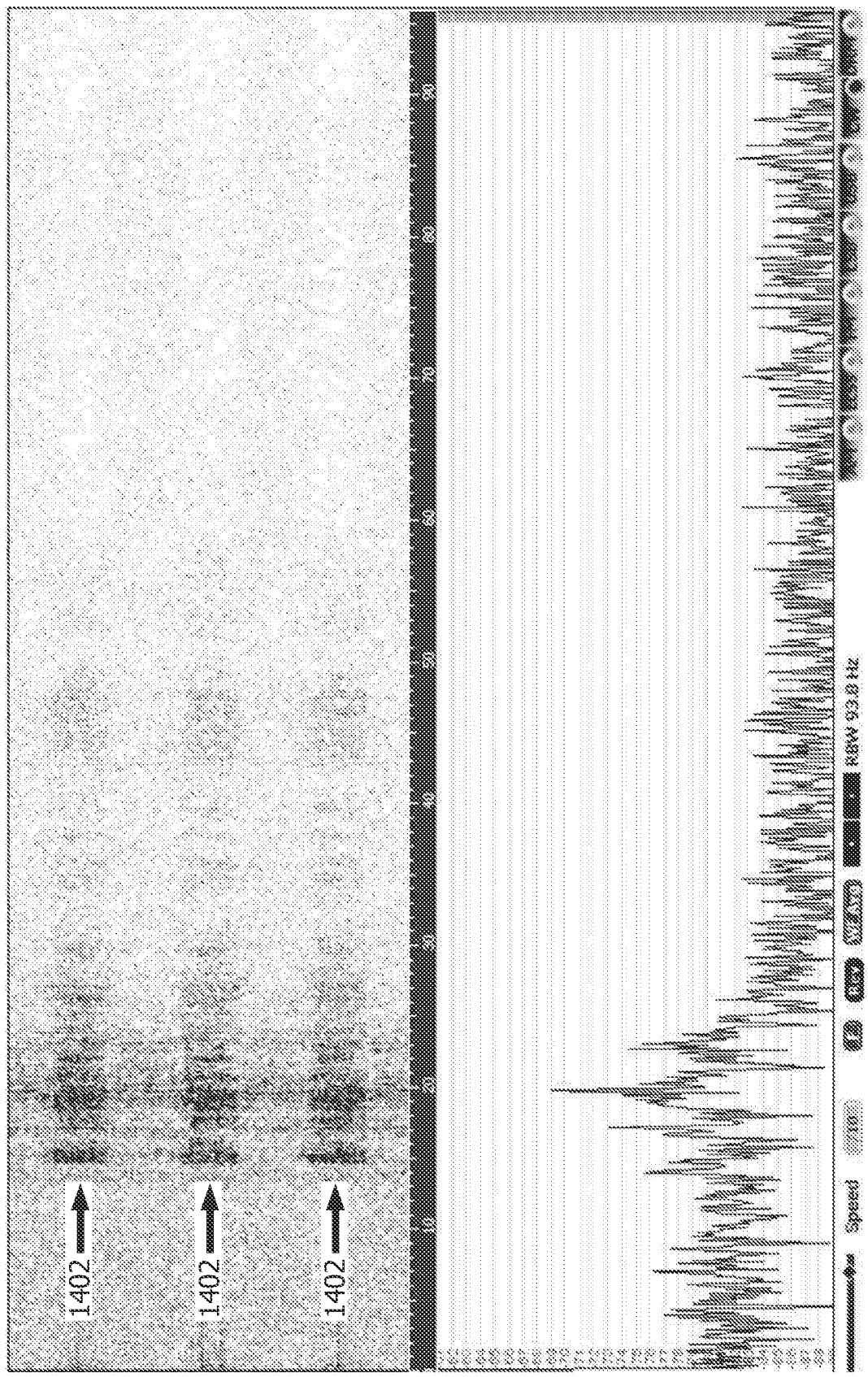
Figure 15:
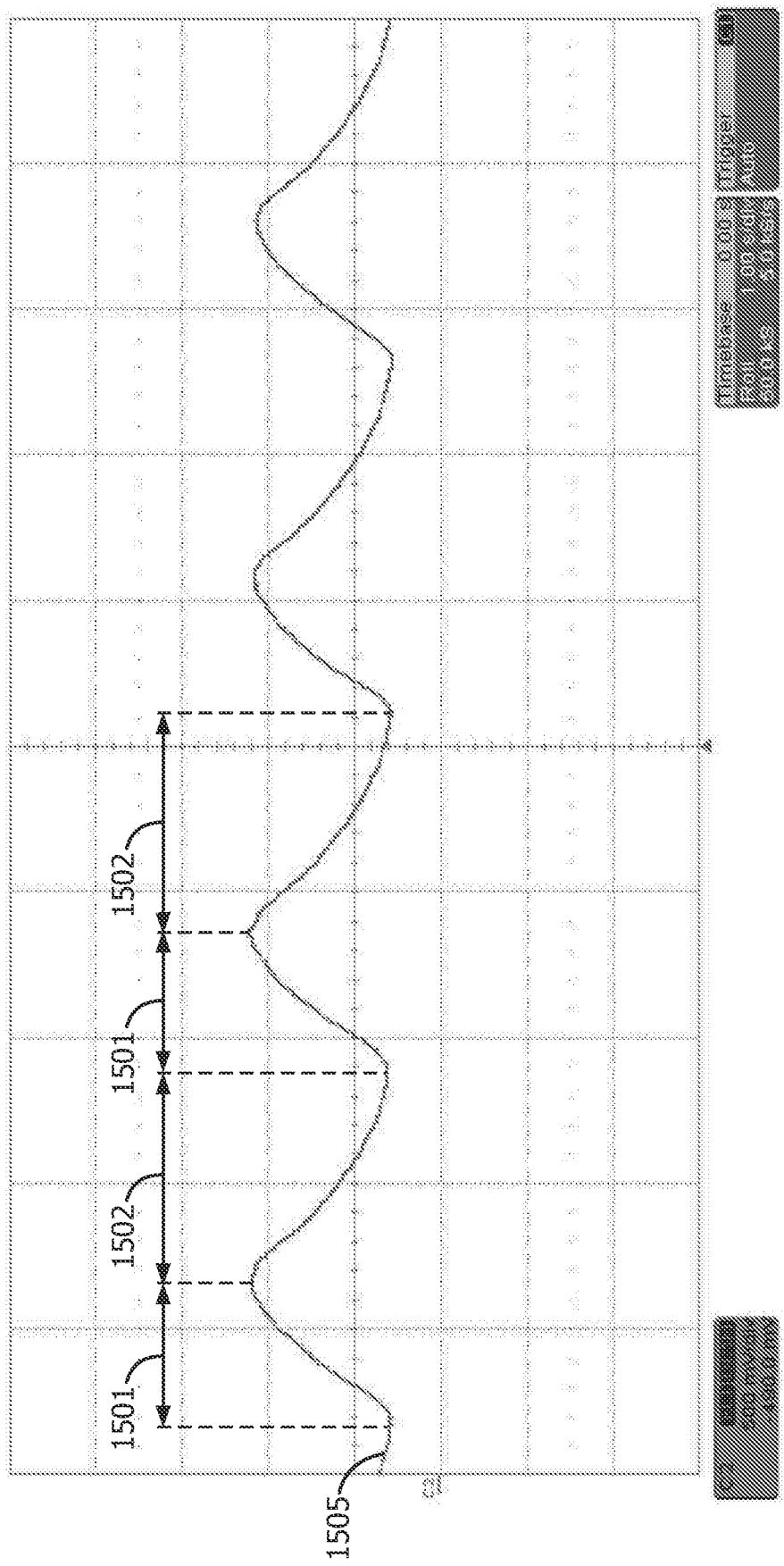
Figure 16:
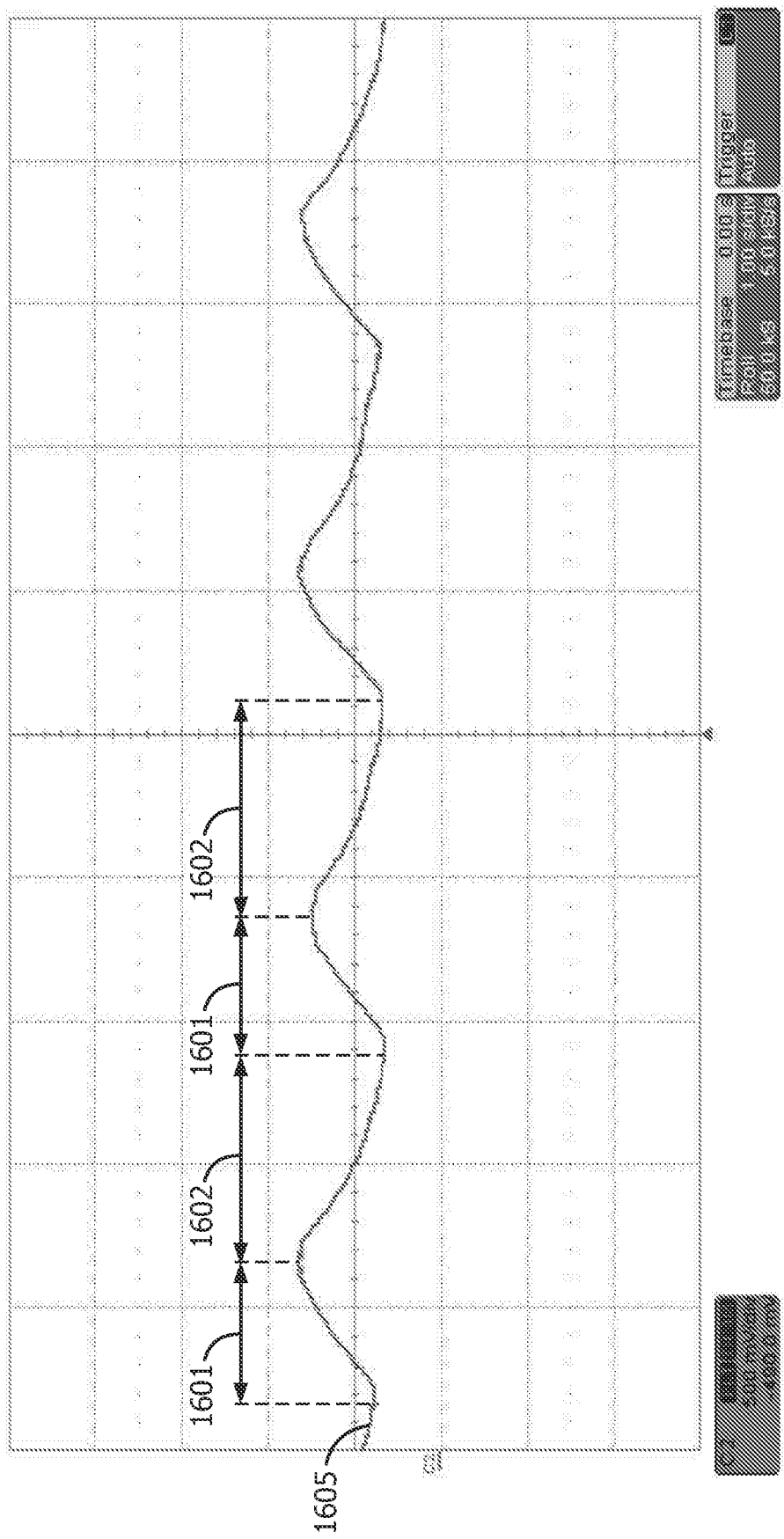

By way of illustration, FIG. 14 illustrates a graph 1400 for energy emitted during the operation of a nebulizer similar to or the same as the nebulizer depicted in FIGS. 8 and 9. Referring to FIG. 14, graph 1400 includes a waterfall display in the top half, and a magnitude (of energy amplitude) in the bottom half. The waterfall display shows time on the vertical axis (as shown here between about 6 and about 10 seconds) and measured frequency (in kHz) on the horizontal axis. Graph 1400 includes a peak magnitude 1401 at a frequency of about 20 kHz. Energy fluctuations 1402 indicate modulations by an inhalation valve. By way of further illustration, FIG. 15 illustrates a graph 1500 depicting voltage signal 1505 as may be produced by subsystem the same as or similar to subsystem 1000 and 1000a (as described elsewhere herein in relation to FIGS. 10 and 11), through frequency-to-voltage circuit 1001 (FIG. 10). Voltage signal 1505 may be produced by measuring, from about a 1 foot distance, ultrasonic energy emitted by a source of ultrasonic energy (similar to or the same as the nebulizer depicted in FIGS. 8 and 9) corresponding to graph 1400 of FIG. 14. Voltage signal 1505 depicts inhalations 1501 and exhalations 1502. By way of further illustration, FIG. 16 illustrates a graph 1600 depicting voltage signal 1605 as may be produced by subsystem the same as or similar to subsystem 1000 and 1000a (as described elsewhere herein in relation to FIGS. 10 and 11), through frequency-to-voltage circuit 1001 (FIG. 10). Voltage signal 1605 may be produced by measuring, from about a 10 foot distance, ultrasonic energy emitted by a source of ultrasonic energy (similar to or the same as the nebulizer depicted in FIGS. 8 and 9) corresponding to graph 1400 of FIG. 14. Voltage signal 1605 depicts inhalations 1601 and exhalations 1602.

Referring to FIG. 1, in some implementations, respiratory medicament delivery device 11 may include a metered-dose inhaler and/or components/features thereof. The emitted ultrasonic energy for meter-dose inhalers may be a (brief) wide-band signal. Such a signal may be measured using a subsystem such as subsystem 1000a in FIG. 11, but with jumper 1021 removed (and resistor R9 changed from 10 kOhm to 2 kOhm), and thereby not using product detector 1007 (FIG. 10) or local oscillator 1020 (FIG. 11). In this mode of operation, the subsystem may be suitable for monitoring wide-band signals between about 15 kHz and about 65 kHz.

Referring to FIG. 1, electronic storage 130 of system 10 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store vectors of parameters based on the generated output signals, and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed by user 108 to system 10 is patient-specific adherence information. An example of information that may be conveyed to user 108 is a report detailing adherence information for subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of parameter determination module 111, control module 112, flow module 113, and/or other modules. Processor 110 may be configured to execute modules 111-113 by software; hardware; firmware; some combination of software, hardware, and/or firmware; and/or other mechanisms for configuring processing capabilities on processor 110.

It should be appreciated that although modules 111-113 are illustrated in FIG. 1 as being co-located within a single processing unit, in embodiments in which processor 110 includes multiple processing units, one or more of modules 111-113 may be located remotely from the other modules. The description of the functionality provided by the different modules 111-113 described herein is for illustrative purposes, and is not intended to be limiting, as any of modules 111-113 may provide more or less functionality than is described. For example, one or more of modules 111-113 may be eliminated, and some or all of its functionality may be incorporated, shared, integrated into, and/or otherwise provided by other ones of modules 111-113. Note that processor 110 may be configured to execute one or more additional modules that may perform some or all of the functionality attributed below to one of modules 111-113.

Parameter determination module 111 of system 10 in FIG. 1 is configured to determine one or more parameters from output signals generated by sensor(s) 142. The one or more parameters may include a first parameter, and/or other parameters. The first parameter may indicate (magnitude of) energy amplitude, e.g. in a first frequency band. For example, the first parameter may indicate the amplitude of the ultrasonic energy received by microphone 142 as described elsewhere herein. In some embodiments, parameter determination module 111 is configured to determine additional (spectral) parameters in a manner similar to the first parameter, though, e.g., corresponding to other frequency bands.

Operation of parameter determination module 111 may be performed in an ongoing manner, for example at a particular sampling rate. The one or more parameters may be determined at different locations and/or positions within system 10 or near subject 106. In some embodiments, parameter determination module 111 may derive vectors of parameters in an ongoing manner during a period of monitoring subject 106. The vectors of the parameters may be based on vectors of generated output signals and/or other (vectors of) determined parameters.

Flow module 113 is configured to determine and/or detect one or more flow changes within respiratory medicament delivery device 11. In some implementations, respiratory medicament delivery device 11 includes valve 16 (FIG. 3), and flow module 113 may be configured to detect one or more flow changes through valve 16. Determinations and/or detections by flow module 113 may be based one or more changes in a parameter determined by parameter determination module 111. In some implementations, the one or more flow changes may be responsive to respiratory actuation by subject 106.

Control module 112 is configured to control respiratory medicament delivery device 11 during operation. Operation of control module 112 may be based on one or more parameters determined by parameter determination module 111 and/or flow module 113. Control by control module 112 may include adjustments, e.g. of the operating frequency (e.g. of the piezoelectric element), drive power, and/or any other adjustable operating conditions as described herein. Adjustments may be based on determined (spectral) parameters and/or generated output signals described elsewhere herein. Adjustments may be made in an ongoing manner, for example at a particular sampling rate. Adjustments may be made in real-time or near-real-time. The rate of adjustment may be milliseconds, 0.5 second, 1 second, 2 seconds, 5 seconds, 10 seconds, 20 seconds, and/or another appropriate rate.

In some implementations, parameter determination module 111 may be configured to determine an adherence metric and/or an adherence parameter for subject 106. The adherence metric and/or adherence parameter may be based on one or more previously described parameters and/or characterizations. For example, a particular adherence metric may be based on a combination of, at least, device actuation information and respiratory timing. An adherence metric and/or adherence parameter may for example be expressed as a percentage of perfect compliance with the recommended treatment. For example, if a particular patient scored a 90% adherence, such a score that may be considered by a care giver in determining a course of action. Alternatively, if a particular patient scored a low percentage of adherence, such a score may be considered relevant before the particular drug is deemed ineffective for that particular patient. Low scores may prompt a change in the chosen type of respiratory device.

In some implementations, parameter determination module 11 may be configured to determine one or more gas parameters and/or respiratory parameters based on determinations and/or detections by flow module 113.

Figure 2:
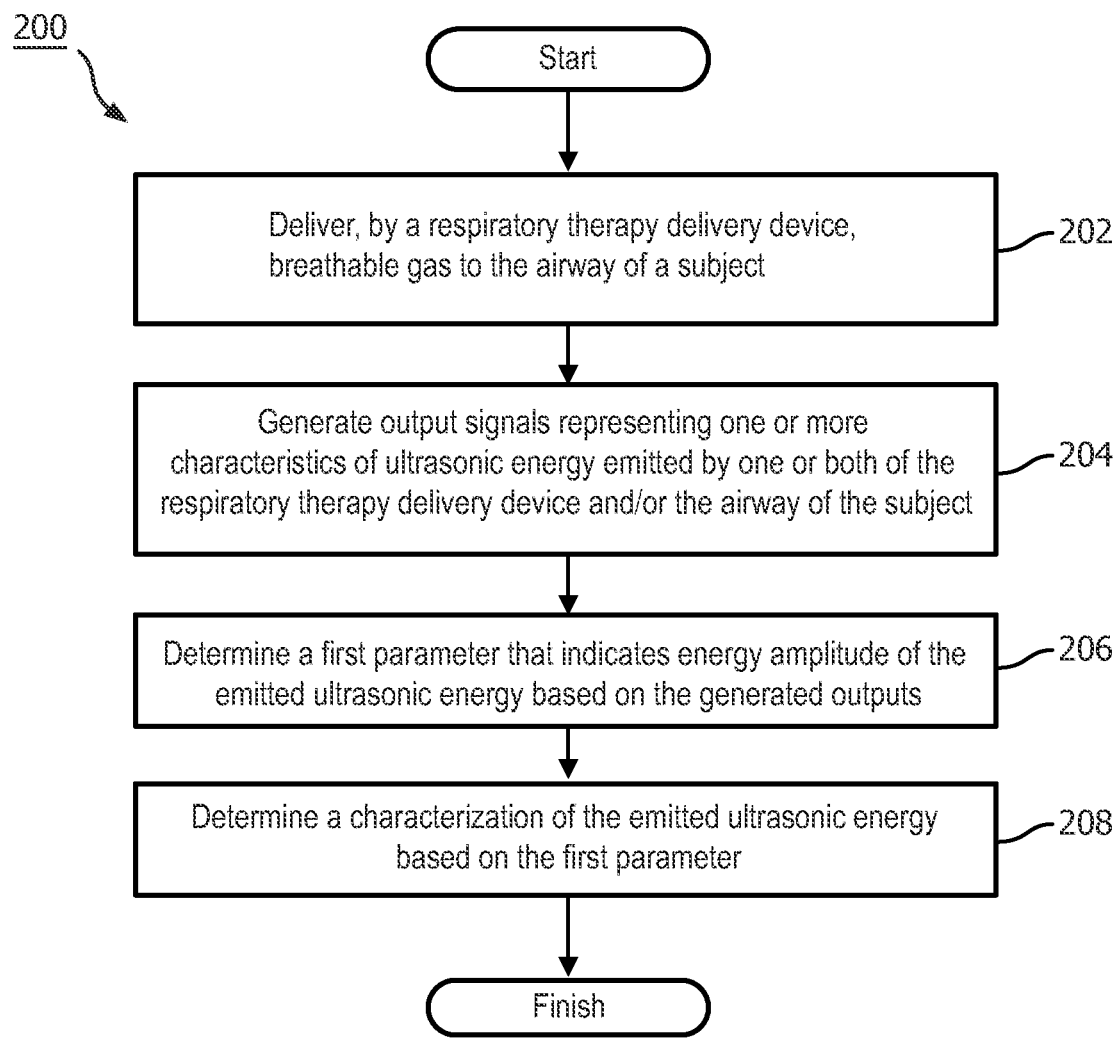
FIG. 2 illustrates a method of delivering medicament to a subject.

FIG. 2 illustrates a method 200 to deliver medicament to a subject, including but not limited to delivery of medicament. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, breathable gas and medicament is combined, by a respiratory medicament delivery device, for delivery to an airway of a subject. The respiratory medicament delivery device includes a valve that opens responsive to respiratory actuation by the subject. In some embodiments, operation 202 is performed by a respiratory medicament delivery device the same as or similar to respiratory medicament delivery device 11 (shown in FIG. 1 and described herein).

At an operation 204, ultrasonic energy is emitted, by a source of ultrasonic energy, at an operating frequency such that at least some emitted ultrasonic energy enters the respiratory medicament delivery device. In some embodiments, operation 204 is performed by a source of ultrasonic energy the same as or similar to source of ultrasonic energy 102 and/or 103 (shown in FIG. 1 and described herein).

At an operation 206, output signals are generated conveying information related to one or more characteristics of the ultrasonic energy emitted by the source of ultrasonic energy. In some embodiments, operation 206 is performed by a sensor the same as or similar to sensor 142 (shown in FIG. 1 and described herein).

At an operation 208, based on the generated output signals, a first parameter is determined that indicates energy amplitude of the emitted ultrasonic energy in a first ultrasonic frequency range. In some embodiments, operation 208 is performed by a parameter determination module the same as or similar to parameter determination module 111 (shown in FIG. 1 and described herein).

At an operation 210, one or more flow changes through the valve are detected based on one or more changes of the first parameter. The one or more flow changes are responsive to respiratory actuation by the subject. In some embodiments, operation 210 is performed by a flow module the same as or similar to flow module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system configured to deliver medicament to a subject, the system comprising:
 a respiratory medicament delivery device configured to combine breathable gas and medicament for delivery to an airway of a subject, wherein the respiratory medicament delivery device includes a valve configured to open responsive to respiratory actuation by the subject;
 a source of ultrasonic energy configured to emit ultrasonic energy such that at least some of the emitted ultrasonic energy enters the respiratory medicament delivery device and to provide energy for combining gas and medicament;
 a sensor configured to generate output signals conveying information related to one or more characteristics of the ultrasonic energy emitted by the source of ultrasonic energy; and
 one or more processors configured to execute computer program modules, the computer program modules comprising:
  a parameter determination module configured to determine, based on the generated output signals, a first parameter that indicates energy amplitude of the emitted ultrasonic energy; and
  a flow module configured to detect one or more flow changes through the valve based on one or more changes of the first parameter, wherein the one or more flow changes are responsive to respiratory actuation by the subject, and wherein the parameter determination module is further configured to determine patient compliance with a recommended treatment based on a combination of device actuation information and respiratory timing.

2. The system of claim 1, wherein the respiratory medicament delivery device includes a piezoelectric element, wherein the piezoelectric element is the source of ultrasonic energy, wherein the valve is an inhalation valve, and wherein the parameter determination module is further configured to determine whether the subject is inhaling through the inhalation valve, and the computer program modules further comprise:
 a control module configured to control the respiratory medicament delivery device during operation through adjustments of the piezoelectric element responsive to determination that the subject is inhaling through the inhalation valve.

3. The system of claim 1, wherein the respiratory medicament delivery device is a metered-dose inhaler, and wherein the parameter determination module is further configured to determine one or more respiratory parameters based on the detected one or more flow changes by the flow module.

4. The system of claim 3, wherein the respiratory medicament delivery device includes a valved holding chamber, and wherein the source of ultrasonic energy is configured to emit ultrasonic energy such that at least some of the emitted ultrasonic energy enters the valved holding chamber.

5. A system configured to deliver medicament to a subject, the system comprising;
 means for combining breathable gas and medicament for delivery to an airway of a subject, wherein the means for combining includes a valve that opens responsive to respiratory actuation by the subject;
 means for emitting ultrasonic energy such that at least some emitted ultrasonic energy enters the means for combining and such that at least some of the energy is provided for combining gas and medicament;
 means for sensing and generating output signals conveying information related to one or more characteristics of the emitted ultrasonic energy;
 means for determining, based on the generated output signals, a first parameter that indicates energy amplitude of the emitted ultrasonic energy; and
 means for detecting one or more flow changes through the valve based on one or more changes of the first parameter, wherein the one or more flow changes are responsive to respiratory actuation by the subject, and wherein the means for determining is further configured to determine patient adherence based on the detected one or more flow changes.

6. The system of claim 5, wherein the means for combining includes a piezoelectric element, wherein the piezoelectric element is the means for emitting ultrasonic energy, wherein the valve is an inhalation valve, and wherein the means for detecting is further configured to determine whether the subject is inhaling through the inhalation valve, the system further comprising:
 means for controlling the means for combining during operation through adjustments of the piezoelectric element, wherein the means for controlling is configured such that adjustments are responsive to the determination that the subject is inhaling through the inhalation valve.

7. The system of claim 5, the system further comprising:
 means for determining one or more respiratory parameters based on the detected one or more flow changes.

8. The system of claim 7, wherein the means for combining includes a valved holding chamber, wherein the means for emitting ultrasonic energy is configured such that at least some emitted ultrasonic energy enters the valved holding chamber.

* * * * *